United States Patent
Manion et al.

(10) Patent No.: US 10,260,082 B2
(45) Date of Patent: Apr. 16, 2019

(54) LIPOSOMAL DETECTION DEVICES AND METHODS FOR THEIR USE AND PREPARATION

(71) Applicant: EMPIRE TECHNOLOGY DEVELOPMENT LLC, Wilmington, DE (US)

(72) Inventors: Michael Keoni Manion, Seattle, WA (US); George Charles Peppou, Hornsby Heights (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 136 days.

(21) Appl. No.: 15/031,710

(22) PCT Filed: Oct. 22, 2013

(86) PCT No.: PCT/US2013/066064
§ 371 (c)(1),
(2) Date: Apr. 22, 2016

(87) PCT Pub. No.: WO2015/060819
PCT Pub. Date: Apr. 30, 2015

(65) Prior Publication Data
US 2016/0265023 A1   Sep. 15, 2016

(51) Int. Cl.
| C12Q 1/04 | (2006.01) |
| G01N 33/58 | (2006.01) |
| G01N 33/84 | (2006.01) |
| C12Q 1/28 | (2006.01) |
| C12Q 1/527 | (2006.01) |
| G01N 33/12 | (2006.01) |

(52) U.S. Cl.
CPC .................. *C12Q 1/04* (2013.01); *C12Q 1/28* (2013.01); *C12Q 1/527* (2013.01); *G01N 33/12* (2013.01); *G01N 33/586* (2013.01); *G01N 33/84* (2013.01); *C12Y 111/01007* (2013.01); *C12Y 401/99001* (2013.01); *G01N 2333/908* (2013.01); *G01N 2333/988* (2013.01)

(58) Field of Classification Search
CPC . C12Q 1/04; C12Q 1/28; C12Q 1/427; G01N 33/586; G01N 33/12; G01N 33/84; G01N 2333/988; G01N 2333/908; C12Y 111/01007; C12Y 401/99001
See application file for complete search history.

(56) References Cited

U.S. PATENT DOCUMENTS

| 4,921,757 A | 5/1990 | Wheatley et al. |
| 5,510,112 A | 4/1996 | Gatt et al. |
| 9,499,852 B2 * | 11/2016 | Jenkins .............. A61K 49/0043 |
| 2001/0012623 A1 * | 8/2001 | Marshall ................. C12Q 1/04 |
| | | 435/34 |
| 2010/0317050 A1 | 12/2010 | Roscoe et al. |
| 2011/0105995 A1 | 5/2011 | Zhu et al. |
| 2013/0064772 A1 | 3/2013 | Swiss et al. |

FOREIGN PATENT DOCUMENTS

| WO | WO-2009038591 A1 * | 3/2009 | .......... A61K 9/5153 |
| WO | 2013093197 A1 | 6/2013 | |

OTHER PUBLICATIONS

Cordeiro et al., Antibacterial Efficacy of Gentamicin Encapsulation in pH-Sensitive Liposomes against an In Vivo *Salmonella enterica* Serovar Typhimurium intracellular Infection Model, Antimicrobial Agents and Chemotherapy (Mar. 2000), 44(3) pp. 533-539.
Hauck et al., Phase I Trial of Doxorubicin-Containing Low Temperature Sensitive Liposomes in Spontaneous Canine Tumors, Clinical Cancer Research (Jul. 1, 2006),12(13) pp. 4004-4010.
International Search Report and Written Opinion for International Application No. PCT/US2013/066064, dated Apr. 16, 2014.
Siragusa and Cutter, Microbial ATP Bioluminescence as a Means to Detect Contamination on Artificially Contaminated Beef Carcass Tissue, Journal of Food Protection (Jul. 1995), 58(7) pp. 764-769.
Xu et al., A Generic Smell Generating Enzymatic Biosensor, Phd Thesis, McMaster University—Chemical Engineering (Sep. 2011), pp. 1-91.
Yatvin et al., pH-Sensitive Liposomes: Possible Clinical Implications, Science (Dec. 12, 1980), 210(4475) pp. 1253-1255.

* cited by examiner

*Primary Examiner* — Renee Claytor
*Assistant Examiner* — Susan E. Fernandez (57) ABSTRACT

Liposomal detection devices and methods of making and using such devices are disclosed. Such liposomal detection devices may be used to detect microbes by detecting a byproduct of microbial metabolism, or may be used to detect changes in pH and/or changes in temperature. Liposomal detection devices may include a first liposome encapsulating a first destabilizing compound and a second liposome encapsulating a second destabilizing compound. The first liposome may destabilize in response to the detection of the target compound or change to release the first destabilizing compound which may destabilize the second liposome. A matrix, such as a hydrogel matrix, may encase the first liposome and the second liposome.

26 Claims, 2 Drawing Sheets

LIPOSOMAL DETECTION DEVICES AND METHODS FOR THEIR USE AND PREPARATION

CROSS-REFERENCE TO RELATED APPLICATIONS

This application is a U.S. national stage filing under 35 U.S.C. § 371 of International Application No. PCT/US2013/066064 filed on Oct. 22, 2013 entitled "LIPOSOMAL DETECTION DEVICES AND METHODS FOR THEIR USE AND PREPARATION," which is incorporated herein by reference in its entirety.

BACKGROUND

Microbial contamination is a challenge for a range of industries including food production, medical and pharmaceutical industries, which often use either aseptic or sterile environments to improve safety. Currently, detection of contamination can be a slow process, taking minutes to hours, and may typically require labor intensive assays or sensors to detect a readout. There exists a need for fast, passive and inexpensive devices and methods to detect microbial contamination.

SUMMARY

Embodiments described in this document are related to a microbial detection device having a first liposome encapsulating a first destabilizing compound, wherein the first liposome destabilizes in response to a byproduct of microbial metabolism to release the first destabilizing compound; a second liposome capable of being destabilized by the first destabilizing compound; and a matrix encasing the first liposome and the second liposome.

Some embodiments are directed to an acid detection device having a first liposome encapsulating a first destabilizing compound, wherein the first liposome destabilizes in the presence of an acid to release the first destabilizing compound; a second acid stable liposome capable of being destabilized by the first destabilizing compound; and a matrix encasing the first liposome and the second liposome.

Some embodiments are directed to a temperature detection device having a first temperature-sensitive liposome encapsulating a first destabilizing compound, wherein the first temperature-sensitive liposome destabilizes in response to a change in temperature to release the first destabilizing compound; a second liposome capable of being destabilized by the first destabilizing compound; and a matrix encasing the first liposome and the second liposome.

Some embodiments are directed to a method of detecting microbial contamination including providing a microbial detection device having a first liposome encapsulating a first destabilizing compound, wherein the first liposome destabilizes in response to a byproduct of microbial metabolism to release the first destabilizing compound; a second liposome capable of being destabilized by the first destabilizing compound; and a matrix encasing the first liposome and the second liposome; detecting a signal transduced by any of the first liposome, the second liposome or a combination thereof in the presence of the byproduct, wherein presence of the signal indicates the presence of at least one microbe.

Some embodiments are directed to a method of making a microbial detection device including providing a first liposome encapsulating a first destabilizing compound, wherein the first liposome destabilizes in response to a byproduct of microbial metabolism to release the first destabilizing compound; providing a second liposome capable of being destabilized by the first destabilizing compound; and encasing the first liposome and the second liposome with a matrix.

Some embodiments are directed to methods of detecting changes in temperature, the method comprising: providing a detection device comprising a first liposome encapsulating a first destabilizing compound, wherein the first liposome destabilizes in response to a change in temperature to release the first destabilizing compound; a second liposome capable of being destabilized by the first destabilizing compound; and a matrix encasing the first liposome and the second liposome; detecting a signal transduced by any of the first liposome, the second liposome or a combination thereof due to the change in temperature, wherein presence of the signal indicates the change in temperature.

Some embodiments are directed to a method of detecting changes in pH, the method comprising providing a detection device comprising: a first liposome encapsulating a first destabilizing compound, wherein the first liposome destabilizes in response to a change in pH to release the first destabilizing compound; a second liposome capable of being destabilized by the first destabilizing compound; and a matrix encasing the first liposome and the second liposome; detecting a signal transduced by any of the first liposome, the second liposome or a combination thereof due to the change in pH, wherein presence of the signal indicates the change in pH.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part of this document. In the drawings, similar symbols typically identify similar components, unless the context dictates otherwise. The illustrative embodiments described in the detailed description, drawings, and claims are not meant to be limiting. Other embodiments may be used, and other changes may be made, without departing from the spirit or scope of the subject matter presented in this document. It will be readily understood that the aspects of the present disclosure, as generally described in this document, and illustrated in the Figures, can be arranged, substituted, combined, separated, and designed in a wide variety of different configurations, all of which are explicitly contemplated to be within the scope of this disclosure.

Generally, the detection devices described herein include a first liposome, or a plurality thereof, encapsulating a first destabilizing compound, wherein the first liposome destabilizes in response to the presence of a triggering event (for example, a byproduct of microbial metabolism, pH, temperature, and so on). The device further includes a second liposome, or plurality thereof, capable of being destabilized by the first destabilizing compound. The second liposome may contain a second destabilizing compound capable of destabilizing the first liposome or a third liposome containing yet another compound. A matrix may also be provided for housing the first and second liposomes.

The second liposome may contain a chemical to destabilize the first liposome, such that the system may self-amplify from an initial activation event. Liposomes may be generated to be sensitive to pH, ionic strength, temperature, or a combination thereof.

In some embodiments, the first and second liposomes may be used to transduce a signal. For example, the first and second liposomes may contain an enzyme and associated substrate, respectively. This signal may, for example, provide a color change, produce an odor, luminesce, produce a voltage, or combinations of these signals. In some embodiments, the microbial detection device is passive. The device may be read passively by the user.

In some embodiments, destabilization of any of the first liposome, the second liposome, or a combination thereof generates an odor. The odor may be generated through the following pathways: indole pathway, cadaverine pathway, putrescine pathway, ester production pathway, volatile sulphur compound-producing pathway, or hydrogen sulphide pathway. In some embodiments, the odor may be generated through the indole pathway. The indole pathway may, for example, have a low odor detection threshold of about 0.6 ppm. The odor detection threshold, as used herein, is the lowest concentration of a compound that is perceivable by the human sense of smell. To facilitate early detection, odors having a lower odor detection threshold are desirable.

In some embodiments, destabilization of any of the first liposome, the second liposome or a combination thereof generates a color change in the matrix. In some embodiments, the signal may include a color change. The color change may be enzymatically mediated or chemically mediated. To induce a color change using chemical means, a two-part system for producing color may be utilized. The two-part system may include isolating two different liposomes, such that upon destabilization of both liposomes, the contents released by both liposomes mix to effect the color change.

The matrix may further include at least one pH sensitive dye. In some embodiments, a pH sensitive dye generates the color change. In some embodiments, destabilization of the first liposome amplifies a pH change mediated by the presence of acid. In some embodiments, the acid is produced during microbial metabolism, and therefore detection of the acid indicates the presence of at least one microbe. In some embodiments, the matrix may include a pH sensitive dye to amplify the pH change mediated by the microbes to generate a color change. Some pH indicators include but are not limited to: gentian violet, malachite green, thymol blue, methyl yellow, bromophenol blue, congo red, methyl orange, bromocresol green, methyl red, azolitmin, bromocresol purple, bromocresol blue, phenol red, neutral red, naphtholphthalein, cresol red, pheonolphthalein, thymolphthalein, alizarine yellow R.

Enzyme-mediated color change may be achieved using a variety of enzymes. For example, horse radish peroxidase efficiently converts colorless substrates (for example, 3,3', 5,5'-Tetramethylbenzidine and 3,3'-Diaminobenzidine) to a colored product. Horseradish peroxidase is a commonly used two-part color change system, which can be used to convert a variety of chromogenic substances (for example 3,3',5,5' tetramethylbenzidine, 3,3'-diaminobenzidine, or 2,2'-azino-bis(3-ethybenzthiazoline-6-sulphonic acid)) into colored products, or even produce light when acting on chemiluminescent substrates (such as ECL), using hydrogen peroxide as the oxidizing agent. Another example of a two part color change system is Factor Xa cleavage of prothrombin chromogenic derivatives, such as S-222. Another commonly used system is alkaline phosphatase reducing tetrazolium salts, such as NBT, MTT, or XTT. These and other two-part color change systems may be employed in various embodiments.

In some embodiments, the devices of embodiments described herein may be encapsulated in a semipermeable membrane. By semipermeable, it is meant that the membrane permits at least the substance to be monitored to pass through while preventing at least some other substances from passing therethrough. Suitable materials for such semipermeable membranes include but are not limited to polyimide, polyamide, cellulose, nitrocellulose, or cellophane membrane, or a combination thereof. Thin film composite membranes could also be used.

In some embodiments, the device may be formed as a continuous material that is cut to size for use (such as, to cover a large table) or manufactured as small, discrete tags that may be applied to any surface or to the inside of a package. The device may be shipped in a sterile package, allowing direct application without risking surface contamination.

In some embodiments, the matrix has a width equal to or less than about 10 μm. In some embodiments, the matrix has a width of about 0.001 μm to about 10 μm, about 0.01 μm to about 10 μm, about 0.1 μm to about 10 μm, about 1 μm to about 10 μm, about 5 μm to about 10 μm, about 8 μm to about 10 μm, or a combination thereof. In some embodiments, the matrix has a width of about 0.001 μm, about 0.01 μm, about 0.1 μm, about 1 μm, about 5 μm, about 8 μm, about 10 μm, or a range between any two of these values.

In some embodiments, the matrix may have a depth of about 0.1 mm to about 10 mm, about 0.5 mm to about 10 mm, about 0.75 mm to about 10 mm, about 1 mm to about 10 mm, about 3 mm to about 10 mm, about 5 mm to about 10 mm, about 7 mm to about 10 mm, or a combination thereof. In some embodiments, the matrix has a depth of about 0.01 mm, about 0.5 mm, about 0.1 mm, about 0.75 mm, about 1 mm, about 3 mm, about 5 mm, about 10 mm, or a range between any two of these values.

Each first liposome, each second liposome, or a combination thereof may have a diameter of about 10 nm to about 50 μm. In some embodiments, each first liposome, each second liposome, or a combination thereof may have a diameter of about 50 nm to about 50 μm, about 100 nm to about 50 μm, about 300 nm to about 50 μm, about 500 nm to about 50 μm, about 1 μm to about 50 μm, about 10 μm to about 50 μm, about 20 μm to about 50 μm, about 30 μm to about 50 μm, about 40 μm to about 50 μm, or a combination thereof. In some embodiments, each first liposome, each second liposome, or a combination thereof may have a diameter of about 50 nm, about 100 nm, about 300 nm, about 500 nm, about 1 μm, about 10 μm, about 20 μm, about 30 μm, about 40 μm, about 50 μm, or a range between any two of these values.

In some embodiments, the detection device has a length of about 5 mm to about 1 m. In some embodiments, the detection device has a length of about 50 mm to about 1 m, about 100 mm to about 1 m, about 300 mm to about 1 m, about 500 mm to about 1 m, about 700 mm to about 1 m. In some embodiments, the detection device has a length of about 5 mm to about 50 mm. In some embodiments, the detection device has a length of about 50 mm to about 100 mm. In some embodiments, the detection device has a length of about 5 mm, about 10 mm, about 20 mm, about 30 mm, about 40 mm, about 50 mm, about 60 mm, about 70 mm, about 80 mm, about 90 mm, about 100 mm, about 300 mm, about 500 mm, about 700 mm, about 1 m or a range between any two of these values In some embodiments, the detection device has a width of about 5 mm to about 1 m. In some embodiments, the detection device has a width of about 50 mm to about 1 m, about 100 mm to about 1 m, about 300 mm to about 1 m, about 500 mm to about 1 m, about 700 mm to about 1 m, or a combination thereof. In some embodiments, the detection device has a length of about 5 mm to about 50 mm. In some embodiments, the detection device has a length of about 50 mm to about 100 mm. In some embodiments, the detection device has a width of about 5 mm, about 10 mm, about 20 mm, about 30 mm, about 40 mm, about 50 mm, about 60 mm, about 70 mm, about 80 mm, about 90 mm, about 100 mm, about 300 mm, about 500 mm, about 700 mm, about 1 m or a range between any two of these values.

In some embodiments, the condition to be detected is contamination, particularly microbial contamination, change in temperature, change in pH, meeting a temperature threshold, meeting a pH threshold, and so on, or a combination thereof.

Some embodiments are directed to a method of detecting a condition including providing a detection device having a first liposome encapsulating a first destabilizing compound, wherein the first liposome destabilizes in response to a byproduct of metabolism to release the first destabilizing compound; a second liposome capable of being destabilized by the first destabilizing compound; and a matrix encasing the first liposome and the second liposome; and detecting a signal transduced by any of the first liposome, the second liposome or a combination thereof in the presence of the byproduct, wherein presence of the signal indicates the presence of at least one microbe.

Some embodiments are directed to a method of making a detection device including providing a first liposome encapsulating a first destabilizing compound, wherein the first liposome destabilizes in response to a byproduct of metabolism to release the first destabilizing compound; providing a second liposome capable of being destabilized by the first destabilizing compound; and encasing the first liposome and the second liposome with a matrix.

Some embodiments of this disclosure are directed to a device for the detection of microbes and methods of making and using such devices. Some embodiments are directed to a device for passive, continuous detection of microbes, either free or biofilm forming, on any surface. As used herein, a microbe refers to a microorganism, which may be a single cell or a multicellular organism and includes prokaryotes, such as bacteria and archaea, protozoa, fungi, algae, green algae, rotifers, planarians, or the like.

Generally, the microbial detection devices described herein include a first liposome, or a plurality thereof, encapsulating a first destabilizing compound, wherein the first liposome destabilizes in response to a byproduct of microbial metabolism to release the first destabilizing compound. The device further includes a second liposome, or plurality thereof, capable of being destabilized by the first destabilizing compound. The second liposome may contain a second destabilizing compound capable of destabilizing the first liposome. A matrix may also be provided for housing the first and second liposomes.

In some embodiments, the microbial detection device may be based on a two liposome system in a matrix. The first liposome may be responsive to one or more byproducts of microbial metabolism (such as acid production, enzyme activity, metabolite production, adenosine triphosphate (ATP) generation, and so on), destabilizing in the presence of these byproducts and releasing the liposomal contents. One or more of the contents of the first liposome may destabilize the second liposome. The second liposome may contain a chemical to destabilize the first liposome, such that the system may self-amplify from an initial activation event. Liposomes may be generated to be sensitive to pH, ionic strength, temperature, or a combination thereof. For example, inclusion of polar lipids may allow the liposome to be sensitive to specific pH. Sensitivity may be achieved through incorporation of charged lipids into the liposomal bilayer such that at a predetermined pH, the charge on the lipid changes, destabilizing the bilayer, and allowing the liposome to lyse. In the case of a temperature sensor, amplification may not be necessary. In this case the sensor could be configured such that the entire or a majority of the material reaches the requisite temperature before the sensor is activated. This would also reduce the likelihood of the sensor triggering during brief thermal events.

In some embodiments, the first and second liposomes may be used to transduce a signal. For example, the first and second liposomes may contain an enzyme and associated substrate, respectively. This signal may, for example, provide a color change, produce an odor, luminesce, produce a voltage, or combinations of these signals. In some embodiments, the microbial detection device is passive. The device may be read passively by the user.

Some embodiments herein are directed to a microbial detection device having a first liposome encapsulating a first destabilizing compound, wherein the first liposome destabilizes in response to a byproduct of microbial metabolism to release the first destabilizing compound; a second liposome capable of being destabilized by the first destabilizing compound; and a matrix encasing the first liposome and the second liposome.

Figure 1:
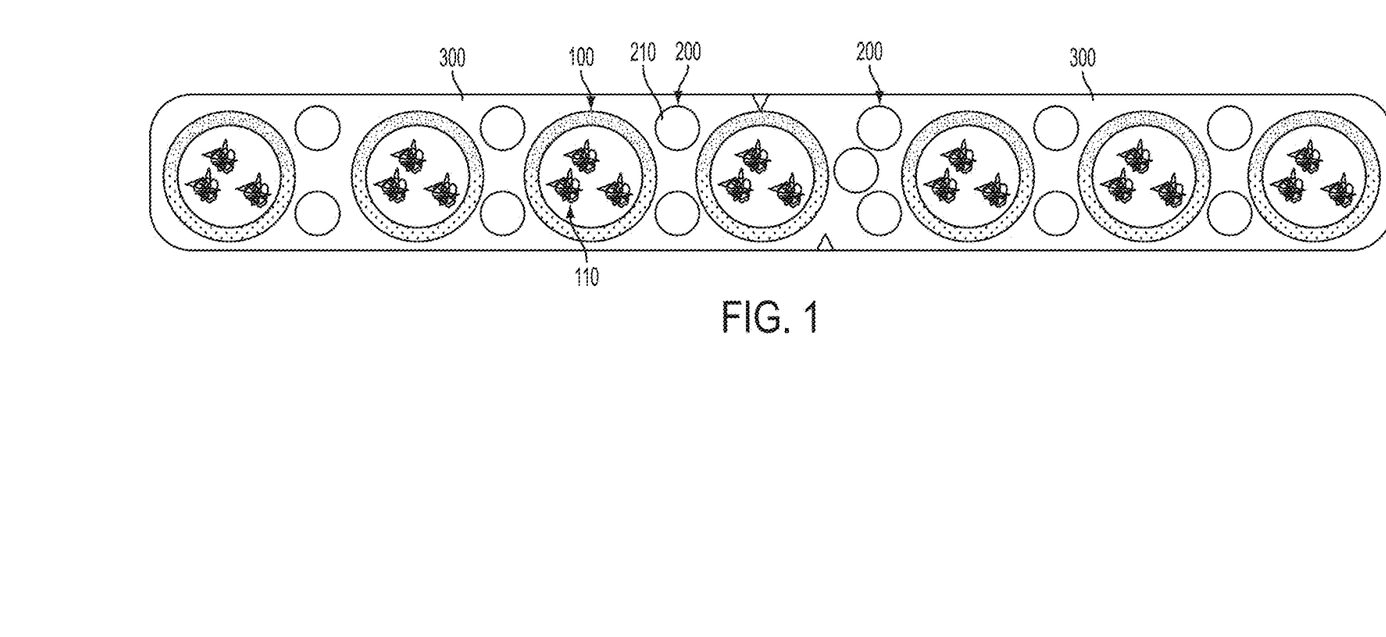
FIG. 1 illustrates an overview of a microbial detection system in accordance with embodiments described herein.

As shown in FIG. 1, a first liposome 100 may contain a first destabilizing compound 110, such as an enzyme, and may be sensitive to a byproduct of microbial metabolism such as an acid. A second liposome 200 may contain acid 210 and may be sensitive to the first destabilizing compound 110 in the first liposome 100. As depicted, a single detection device can have a plurality of first liposomes and a plurality of second liposomes. The first and second liposomes may be embedded, encased, or otherwise disposed in a matrix 300. The structure of FIG. 1, thus, may be capable of detecting acid produced during microbial metabolism.

Figure 2:
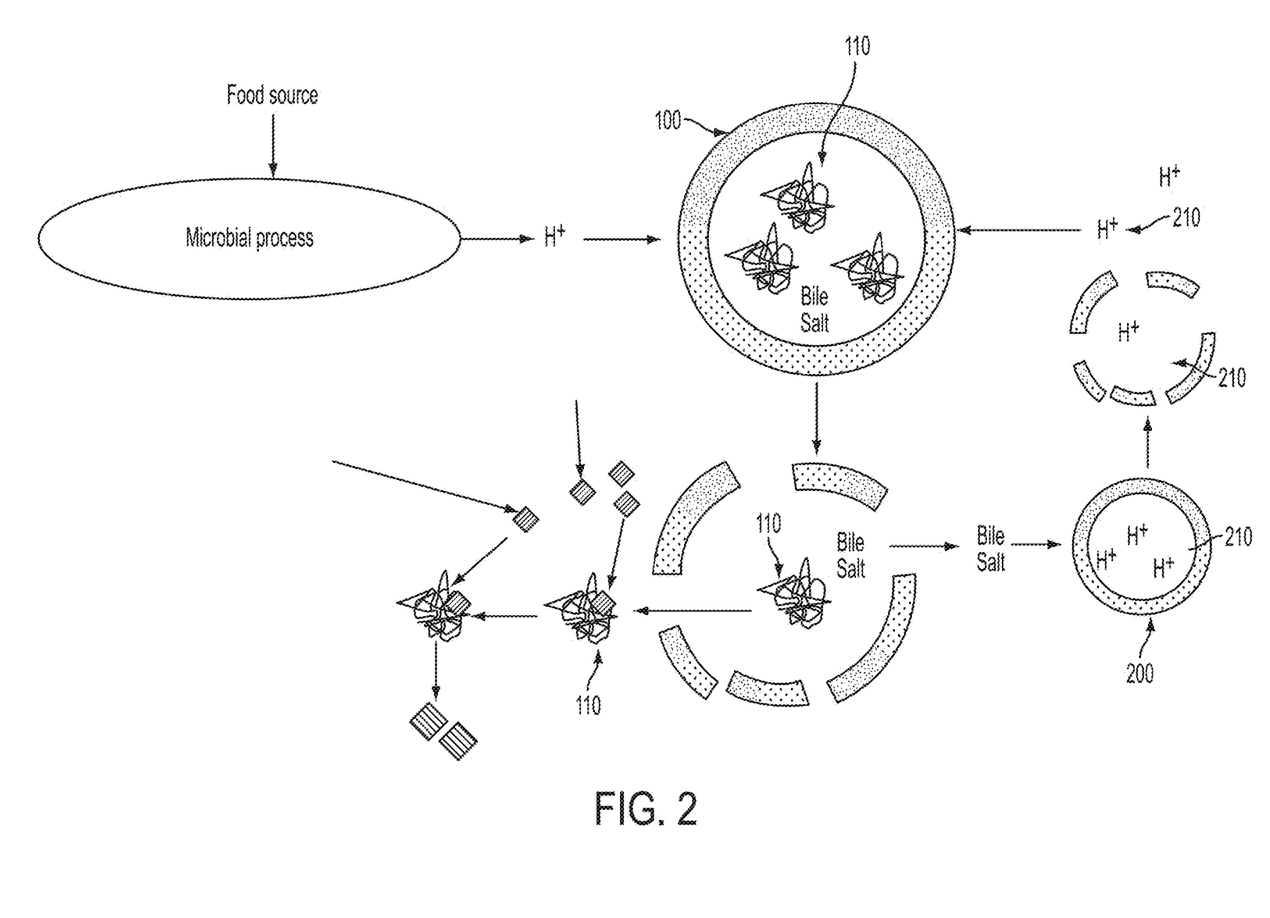
FIG. 2 illustrates an exemplary microbial detection system in accordance with embodiments described herein, employing an indole pathway of odor generation.

As shown in FIG. 2, a device for detecting acid producing bacteria has a glucose food source provided in the matrix, which allows for the growth of bacteria. The bacterial growth produces an acid byproduct which destabilizes the first liposome 100, releasing its liposomal contents 110. In one embodiment, the first liposome 100 contains tryptophanase and bile salts. The tryptophanase undergoes an indole pathway to create an odor. The first liposome may also release bile salts, which destabilize the second acid-containing liposome thereby activating a self-amplifying process wherein the cycle repeats, in this instance, to produce a detectable odor as a signal of bacterial presence.

In some embodiments, the byproduct may include an acid, an enzyme, a metabolite, adenosine triphosphate (ATP), a lipid, or a combination thereof. In some embodiments, the first destabilizing compound may include a bile salt, a lipase, an acid, a base, a cardiolipin, a reactant capable of generating heat through exothermic reaction, a surfactant, an ethanol, or a combination thereof.

In some embodiments, the second liposome encapsulates a second destabilizing compound capable of destabilizing the first liposome. In some embodiments, the second liposome releases the second destabilizing compound when the second liposome is destabilized. The second destabilizing compound may be selected from a bile salt, a lipase, an acid, a base, a cardiolipin, a reactant capable of generating heat through exothermic reaction, a surfactant, an ethanol, or a combination thereof.

In some embodiments, any of the first liposome, the second liposome, or a combination thereof is capable of transducing a signal in the presence of at least one microbe. The signal of embodiments herein may be a color, an odor, a luminescence, a voltage, or a combination thereof.

In some embodiments, the matrix houses a plurality of the first liposome and a plurality of the second liposome. The liposomes may be housed on, within, or partially within the matrix. In some instances, the liposomes are encased or enveloped by the matrix. The matrix of embodiments herein may include a hydrogel matrix, a polymer matrix, a polysaccharide matrix, a peptide matrix or a combination thereof. The matrix may further include agarose, acrylamide gel, gelatin, hyaluronans, chitosans, alginates, collagen, dextran, pectin, carrageenan, polylysine, or a combination thereof. In some embodiments, the matrix is a hydrogel matrix. The hydrogel matrix may be formed of a high water content polymer hydrogel such as, agarose.

In some embodiments, the matrix may further include a microbial food source. In some embodiments, the microbial food source is selected from carbon, nitrogen or a combination thereof. In some embodiments, the hydrogel matrix may contain a small amount of a carbon source for bacteria to metabolize, such that the bacteria will preferentially grow on the matrix. This may allow for earlier detection of microbes, as microbes may grow more readily on the matrix than surrounding material. Long term liposome stability may be improved by embedding the liposome in the hydrogel. Varying the carbon source contained in the matrix and other components may allow for selective detection of certain strains of bacteria. For example, upon inclusion of antibiotics into the matrix, the microbial detection device will only be activated by antibiotic resistant bacteria.

Some forms of bacteria are known to have a hemolytic function, disrupting red blood cells in the body. Microbes displaying such hemolytic functionality may be capable of activating any of the tags, due to non-specific liposome disruption.

In some embodiments, the matrix may further include an antibiotic, a nutrient, an antimicrobial, a pH sensitive dye, or a combination thereof. The matrix may be adapted for selective growth of a single type of microbe or multiple types of microbes to be detected. In some embodiments, the first liposome is unilamellar or multilamellar. In some embodiments, second liposome is unilamellar or multilamellar. In some embodiments, the first and/or second liposomes are unilamellar.

Activation threshold and microbial specificity of the microbial detection devices of embodiments herein may be selected through choice of matrix and the liposomes employed. The matrix contents may be selected based on carbon source, buffer conditions, and/or, selective factors such as biocides or antimicrobials, for example, to select for antibiotic resistant strains; antimicrobial peptides or compounds used to select for Gram positive and/or negative strains; antibacterials, antifungals, antivirals, and the like can be used to negatively select for other microbes; and other selective factors. The particular liposomes used can be based on the desired specificity and sensitivity as well as the desired destabilizing compound and detection environment.

The microbial detection device may be incorporated into a number of finished structures or detection devices to allow different applications. The matrix of the microbial detection device may be placed directly onto the surface to be monitored. For example, a detection device as described herein may be incorporated into or onto walls, furniture, coolers, refrigerators, freezers, food packaging, medical packaging, paper products, containers, storage containers, shipping vessels, and so on.

The sensitivity of the microbial detection device may be adjusted to sense extremely low concentrations of microbes (applicable to pharmaceutical processing) up to the extremely high concentrations of microbes such as those present in biofilms. Accordingly, the applications for microbial detection devices include industries such as healthcare, food production and pharmaceutical production.

The microbial detection device of embodiments described herein may also be used as an indicator, in which multiple liposomes with different sensitivities in a single tag package allow for detection of the presence of a specific microbial concentration. For aseptic conditions this may be preferred, as some microbial load would be permissible.

Some embodiments are directed to a method of detecting microbial contamination including providing a microbial detection device having a first liposome encapsulating a first destabilizing compound, wherein the first liposome destabilizes in response to a byproduct of microbial metabolism to release the first destabilizing compound; a second liposome capable of being destabilized by the first destabilizing compound; and a matrix encasing the first liposome and the second liposome; and detecting a signal transduced by any of the first liposome, the second liposome or a combination thereof in the presence of the byproduct, wherein presence of the signal indicates the presence of at least one microbe.

Some embodiments are directed to a method of making a microbial detection device including providing a first liposome encapsulating a first destabilizing compound, wherein the first liposome destabilizes in response to a byproduct of microbial metabolism to release the first destabilizing compound; providing a second liposome capable of being destabilized by the first destabilizing compound; and encasing the first liposome and the second liposome with a matrix.

Some embodiments are directed to a temperature detection device having a first temperature-sensitive liposome encapsulating a first destabilizing compound, wherein the first temperature-sensitive liposome destabilizes in response to a change in temperature to release the first destabilizing compound; a second liposome capable of being destabilized by the first destabilizing compound; and a matrix encasing the first liposome and the second liposome. Use of temperature-sensitive liposomes may provide a passive measure of small changes in temperature. The temperature-sensitive liposomes may be sensitive to changes in temperatures that are close to biological temperatures, or other temperature ranges depending on the desired detection. The temperature detection device may be used to detect changes in temperature of an environment, for example a temperature change resulting from microbial metabolism, a temperature change due to climate, or other causes of temperature fluctuations in the environment.

In some embodiments, at least one of the first liposome and the second liposome may be a temperature-sensitive liposome. In some embodiments, at least one of the first liposome and the second liposome may include a charged lipid, a polar lipid, or a combination thereof. The charged lipid or polar lipid may be a fatty acid, glycerolipid, glycerophospholipid, sphingolipid, sterol lipid, prenol lipid, saccharolipid or a polyketide. Exemplary charged or polar lipids include but are not limited to N,N-dioleyl-N,N-dimethylammonium chloride ("DODAC"); N-(2,3-dioleyloxy) propyl)-N,N,N-trimethylammonium chloride ("DOTMA"); N,N-distearyl-N,N-dimethylammonium bromide ("DDAB"); N-(2,3-dioleyloxy)propyl)-N,N,N-trimethylammonium chloride ("DOTAP"); 3β-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"), N-(2,3-dioleyloxy)propyl)-N,N-dimethylammonium chloride ("DODMA") and 1,2-Dioleoyl-3-dimethylammonium-propane ("DODAP"), phosphatidyl inositol, phosphatidyl serine, phosphatidyl glycerol, phosphatidic acid, diphosphatidyl glycerol, poly (ethylene glycol)-phosphatidyl ethanolamine, dimyristoylphosphatidyl glycerol, dioleoylphosphatidyl glycerol, dilauryloylphosphatidyl glycerol, dipalmitoylphosphatidyl glycerol, distearyloylphosphatidyl glycerol, dimyristoyl phosphatic acid, dipalmitoyl phosphatic acid, dimyristoyl phosphatidyl serine, dipalmitoyl phosphatidyl serine, brain phosphatidyl serine, diacylphosphatidylcholine, diacylphosphatidylethanolamine, ceramide, sphingomyelin, cephalin, cholesterol, cerebrosides and diacylglycerols, PEG-lipids or polyamide oligomer-lipids, PEG-ceramides, Lipofectin™ (commercially available cationic liposomes comprising DOTMA and 1,2-dioleoyl-sn-3-phosphoethanolamine ("DOPE"), from GIBCO/BRL, Grand Island, N.Y., USA); Lipofectamine™ (commercially available cationic liposomes comprising N-(1-(2,3-dioleyloxy)propyl)-N-(2-(sperminecarboxamido)ethyl)-N,N-dimethylammonium trifluoroacetate ("DOSPA") and DOPE from GIBCO/BRL); and Transfectam™ (commercially available cationic lipids comprising dioctadecylamidoglycyl carboxyspermine ("DOGS") in ethanol from Promega Corp., Madison, Wis., USA).

Some embodiments are directed to a method of detecting temperature or temperature change including providing a detection device having a first liposome encapsulating a first destabilizing compound, wherein the first liposome destabilizes in response to a byproduct of metabolism to release the first destabilizing compound; a second liposome capable of being destabilized by the first destabilizing compound; and a matrix encasing the first liposome and the second liposome; and detecting a signal transduced by any of the first liposome, the second liposome or a combination thereof in the presence of the byproduct, wherein presence of the signal indicates a threshold temperature or temperature change has been met.

Some embodiments are directed to a method of making a detection device including providing a first liposome encapsulating a first destabilizing compound, wherein the first liposome destabilizes in response to achieving a temperature threshold or a change in temperature to release the first destabilizing compound; providing a second liposome capable of being destabilized by the first destabilizing compound; and encasing the first liposome and the second liposome with a matrix.

In some embodiments, the matrix may further include at least one pH buffer. In some embodiments, the amount and type of buffer used affects the amount of acid production required to induce a response in the device. In some embodiments, modulating this threshold may allow the microbial load that activates the device to be varied. Suitable pH buffers include, but are not limited to citric acid, acetic acid, dipotassium phosphate, N-cyclohexyl-2-aminoethanesulfonic acid, N-Tris(hydroxymethyl)methyl-3-aminopropanesulfonic acid ("TAPS"), bicine, tris(hydroxymethyl)aminomethane ("Tris"), tricine, 3-[N-Tris(hydroxymethyl)methylamino]-2-hydroxypropanesulfonic acid ("TAPSO"), 4-(2-hydroxyethyl)-1-piperazineethanesulfonic acid ("HEPES"), 2-[[1,3-dihydroxy-2-(hydroxymethyl)propan-2-yl]amino]ethanesulfonic acid ("TES"), 3-morpholinopropane-1-sulfonic acid ("MOPS"), 1,4-Piperazinediethanesulfonic acid ("PIPES"), cacodylate, saline-sodium citrate ("SSC"), 2-(N-morpholino)ethanesulfonic acid ("MES"), succinic acid, and combinations thereof.

Some embodiments are directed to an acid detection device including a first liposome encapsulating a first destabilizing compound, wherein the first liposome destabilizes in the presence of an acid to release the first destabilizing compound; a second acid stable liposome capable of being destabilized by the first destabilizing compound; and a matrix encasing the first liposome and the second liposome. In some embodiments, the second acid stable liposome encapsulates at least one acid capable of destabilizing the first liposome. The acid detection device may be used to detect changes in an acid level of an environment, for example an increase in acid level resulting from microbial metabolism, acid rain, acid spillage from a nearby vessel, or other causes. In some embodiments, the acid detection device may be used to detect acid-producing bacteria.

The term "acid-producing bacteria" is generally used to refer to any prokaryotic microorganisms that are characterized by their production of acid as a major metabolic end-product of carbohydrate fermentation. Examples of acid-producing bacteria include, but are not limited to, *Acetobacter* and LAB. The most common acid-producing bacteria include lactic acid-producing bacteria. The term "lactic acid-producing bacteria" or "LAB" is generally used to refer to any prokaryotic microorganisms that are characterized by their production of lactic acid as a major metabolic end-product of carbohydrate fermentation. Examples of lactic acid bacteria include, but are not limited to, members of the following genera—*Streptococcus, Enterococcus, Lactobacillus, Pediococcus, Lactococcus, Aerococcus, Carnobacterium, Oenococcus, Sporolactobacillus, Teragenococcus, Vagococcus*, and *Weisella*. Lactic acid bacteria include certain pathogenic bacteria such as, for example, vancomycin-resistant *Enterococcus*, certain species of the genus *Leuconostoc*, and *Streptococcus pyogenes*. Environmental factors that may affect the growth of acid-producing bacteria can include the presence or absence of nutrients, pH, moisture content, oxidation-reduction potential, antimicrobial compounds, temperature, atmospheric gas composition and biological structures or barriers.

Some embodiments are directed to a method of detecting acid and/or pH change including providing a detection device having a first liposome encapsulating a first destabilizing compound, wherein the first liposome destabilizes in response to pH to release the first destabilizing compound; a second liposome capable of being destabilized by the first destabilizing compound; and a matrix encasing the first liposome and the second liposome; and detecting a signal transduced by any of the first liposome, the second liposome or a combination thereof in the presence of the byproduct, wherein presence of the signal indicates the presence of acid or a pH change.

Some embodiments are directed to a method of making an acid detection device including providing a first liposome encapsulating a first destabilizing compound, wherein the first liposome destabilizes in response to pH to release the first destabilizing compound; providing a second liposome capable of being destabilized by the first destabilizing compound; and encasing the first liposome and the second liposome with a matrix.

Additional elements may also be added to the liposomes to provide additional properties such as antimicrobials, nutrients, antibiotics, peptides, proteins, salts, carbohydrates, inorganic compounds, organic compounds, cholesterol, glycoproteins, glycolipids, lipids, or the like.

EXAMPLES

Example 1: A Microbial Detection Device Sensitive to Acid Producing Bacteria

A lab bench surface contains a microbial detection device, wherein the device includes a first liposome 100 which is sensitive to acid and which contains tryptophanase and bile salts 110, and a second liposome 200 which is sensitive to bile salts and which contains acid 210. See FIG. 2. The liposomes 100, 200 are encased in a hydrogel matrix 300 composed of agarose which attaches the device to the lab bench surface. Upon exposure to acid-producing bacteria, such as *Acetobacter aceti*, the first liposome ruptures, releasing its contents. The tryptophanase undergoes an indole pathway producing an odor to alert workers that there is microbial contamination. The release of bile salts destabilizes the second liposome and the second liposome ruptures releasing acid, thereby activating other first liposomes in the device and self-amplifying the alerting signal of the odor.

*Acetobacter aceti* is implicated in the spoilage of wine and thus the microbial detection device may be used in a winery to detect contamination of the wine before spoilage occurs.

Example 2: A Microbial Detection Device Sensitive to Temperature

A microbial detection device is attached to a wall, wherein the device includes a first temperature-sensitive liposome, which is sensitive to temperature changes, and encapsulates ethanol and horse radish peroxidase; and a second liposome, which is sensitive to ethanol and which encapsulates 3,3',5,5'-Tetramethylbenzidine (TMB) and a reactant capable of generating heat through exothermic reaction. Candidate reactants include a base (to neutralize acid already present) such as sodium hydroxide (NaOH), potassium hydroxide (KOH), barium hydroxide ($Ba(OH)_2$), cesium hydroxide (CsOH), strontium hydroxide ($Sr(OH)_2$), calcium hydroxide ($Ca(OH)_2$), lithium hydroxide (LiOH), and rubidium hydroxide (RbOH). Other possible reactions include hydration of anhydrous compounds (such as copper (II) sulfate, calcium oxide, or calcium chloride), polymerization reactions, or oxidation reactions (such as catalyzed oxidation of iron). A gelatin matrix encases the first liposome and the second liposome and attaches the device to the wall. Upon exposure to a predetermined change in temperature, for example, due to microbial contamination, the temperature-sensitive first liposome will rupture releasing ethanol and horse radish peroxide. The ethanol will destabilize the second liposome, rupturing it and mixing the horse radish peroxide with the TMB, causing a color change. The rupture of the second liposome releases the reactant capable of generating heat through exothermic reaction, thereby self-amplifying the color change signal.

Example 3: An Acid Detection Device for Use in an Industrial Environment

An acid detection device is attached to a wall, wherein the device includes a first temperature-sensitive liposome, which is sensitive to acid or acid vapors of pH 3 or lower, and encapsulates ethanol and thiocyanate ions ($SCN^-$); and a second liposome, which is sensitive to ethanol and encapsulates iron (III) ions ($Fe^{3+}$). A gelatin matrix encases the first liposome and the second liposome and attaches the device to the wall.

The first liposome destabilizes and releases the colorless thiocyanate ions ($SCN^-$) when exposed to acid or acid vapors of pH 3 or lower. As the reaction continues and the second liposome is destabilized, iron (III) ions ($Fe^{3+}$) are released, which normally exhibits a light yellow color. The thiocyanate ion ($SCN^-$) and the $Fe^{3+}$ react together to produce a blood-red color, indicating to those nearby the detection of acid or acid vapors of pH 3 or lower.

The acid detection device provides an immediate visual indication of a spill or leak, often at quantities that are too small to trigger an exposure with conventional detection devices. The device may be used on potentially hazardous surfaces such as valves, pipes, pumps, flanges, tanks, sample ports, flow indicators, expansion joints, weld sites, clamps, hose connections, truck tanker or tanker car domes, threaded connections, or any place where an accidental leak or spill may occur.

Example 4: A Temperature Sensitive Detection Device for the Food Industry

A temperature sensitive device attaches to a packaging for meat. The device includes a first liposome encapsulating an acid and a chromophore, where the first liposome is sensitive to temperatures above 40° F. (4° C.), and a second liposome which is sensitive to acid and which encapsulates a reactant capable of generating heat through exothermic reaction. Candidate reactants include a base (to neutralize acid already present) such as sodium hydroxide (NaOH), potassium hydroxide (KOH), barium hydroxide ($Ba(OH)_2$), cesium hydroxide (CsOH), strontium hydroxide ($Sr(OH)_2$), calcium hydroxide ($Ca(OH)_2$), lithium hydroxide (LiOH), and rubidium hydroxide (RbOH). Other possible reactions include hydration of anhydrous compounds (such as copper (II) sulfate, calcium oxide, or calcium chloride), polymerization reactions, or oxidation reactions (such as catalyzed oxidation of iron). A gelatin matrix encases the first liposome and the second liposome and attaches the device to the packaging.

The first liposome destabilizes and releases the chromophore and acid when exposed to temperatures above 40° F. (4° C.). As the second liposome is destabilized by the acid, the reactant capable of generating heat through exothermic reaction is released, causing a self-amplification of the signal.

The present disclosure is not to be limited in terms of the particular embodiments described in this application, which are intended as illustrations of various aspects. Many modifications and variations can be made without departing from its spirit and scope, as will be apparent to those skilled in the art. Functionally, equivalent methods and apparatuses within the scope of the disclosure, in addition to those enumerated in this document, will be apparent to those skilled in the art from the foregoing descriptions. Such modifications and variations are intended to fall within the scope of the appended claims. The present disclosure includes the full scope of equivalents to which the claims are entitled. It is to be understood that this disclosure is not limited to particular methods, reagents, compounds, compositions or biological systems, which can, of course, vary. It is also to be understood that the terminology used in this document is for the purpose of describing particular embodiments only, and is not intended to be limiting.

With respect to the use of substantially any plural and/or singular terms in this document, those having skill in the art can translate from the plural to the singular and/or from the singular to the plural as is appropriate to the context and/or application. The various singular/plural permutations may be expressly set forth in this document for sake of clarity.

It will be understood by those within the art that, in general, terms used in this document, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," and so on). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, and so on" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, and so on). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed in this document also encompass any and all possible subranges and combinations of subranges thereof. Any listed range can be easily recognized as sufficiently describing and enabling the same range being broken down into at least equal halves, thirds, quarters, fifths, tenths, and so on. As a non-limiting example, each range discussed in this document can be readily broken down into a lower third, middle third and upper third, and so on. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 bonds refers to groups having 1, 2, or 3 bonds. Similarly, a group having 1-5 bonds refers to groups having 1, 2, 3, 4, or 5 bonds, and so forth.

From the foregoing, it will be appreciated that various embodiments of the present disclosure have been described in this document for purposes of illustration, and that various modifications may be made without departing from the scope and spirit of the present disclosure. Accordingly, the various embodiments disclosed in this document are not intended to be limiting, with the true scope and spirit being indicated by the following claims.

What is claimed is:

1. A microbial detection device comprising:
    a first liposome encapsulating a first destabilizing compound, wherein the first liposome destabilizes in response to a byproduct of microbial metabolism to release the first destabilizing compound from the first liposome;
    a second liposome capable of being destabilized by the first destabilizing compound released from the first liposome, wherein the second liposome encapsulates a second destabilizing compound capable of destabilizing the first liposome when the second liposome is destabilized and releases the second destabilizing compound, wherein the second destabilizing compound is different than the first destabilizing compound; and
    a matrix encasing the first liposome and the second liposome.

2. The microbial detection device of claim 1, wherein the byproduct comprises an acid, an enzyme, a metabolite, adenosine triphosphate (ATP), a lipid, or a combination thereof.

3. The microbial detection device of claim 1, wherein the first destabilizing compound comprises a bile salt, a lipase, an acid, a base, a cardiolipin, a reactant capable of generating heat through exothermic reaction, a surfactant, ethanol, or a combination thereof.

4. The microbial detection device of claim 1, wherein the second destabilizing compound is selected from a bile salt, a lipase, an acid, a base, a cardiolipin, a reactant capable of generating heat through exothermic reaction, a surfactant, ethanol, or a combination thereof.

5. The microbial detection device of claim 1, wherein the matrix encases a plurality of the first liposome and a plurality of the second liposome.

6. The microbial detection device of claim 1, wherein any of the first liposome, the second liposome, or a combination thereof is capable of transducing a signal in a presence of at least one microbe, wherein the signal includes a color, an odor, a luminescence, a voltage, or a combination thereof.

7. The microbial detection device of claim 1, wherein the matrix is a hydrogel matrix, a polymer matrix, a polysaccharide matrix, a peptide matrix, or a combination thereof.

8. The microbial detection device of claim 1, wherein the matrix further comprises a microbial food source, an antibiotic, a nutrient, an antimicrobial, a pH sensitive dye, or a combination thereof.

9. The microbial detection device of claim 1, wherein at least one of the first liposome or the second liposome is unilamellar or multilamellar.

10. The microbial detection device of claim 1, wherein at least one of the first liposome or the second liposome is a temperature-sensitive liposome.

11. The microbial detection device of claim 1, wherein at least one of the first liposome or the second liposome comprises a charged lipid, a polar lipid, or a combination thereof.

12. The microbial detection device of claim 1, wherein the matrix further comprises at least one pH buffer.

13. A method of detecting microbial contamination, the method comprising:
    providing a microbial detection device comprising:
        a first liposome encapsulating a first destabilizing compound, wherein the first liposome destabilizes in response to a byproduct of microbial metabolism to release the first destabilizing compound from the first liposome;
        a second liposome capable of being destabilized by the first destabilizing compound released from the first liposome, wherein the second liposome encapsulates a second destabilizing compound capable of destabilizing the first liposome when the second liposome is destabilized and releases the second destabilizing compound, wherein the second destabilizing compound is different than the first destabilizing compound;
        and
        a matrix encasing the first liposome and the second liposome;
    detecting a signal transduced by any of the first liposome, the second liposome, or a combination thereof in presence of the byproduct, wherein presence of the signal indicates a presence of at least one microbe.

14. The method of claim 13, wherein detecting a signal comprises detecting a signal including a color, an odor, a luminescence, a voltage, or a combination thereof.

15. The method of claim 13, wherein providing the microbial detection device comprises providing the matrix including a plurality of the first liposome or a plurality of the second liposome.

16. The method of claim 13, wherein providing the microbial detection device comprises providing the first liposome encapsulating the first destabilizing compound including a bile salt, a lipase, an acid, a base, a cardiolipin, a reactant capable of generating heat through exothermic reaction, surfactant, ethanol, or a combination thereof.

17. The method of claim 13, wherein providing the microbial detection device comprises providing the matrix including a hydrogel matrix, a polymer matrix, a polysaccharide matrix, a peptide matrix, or a combination thereof.

18. The method of claim 13, wherein providing the microbial detection device comprises providing the first liposome or the second liposome including a charged lipid, a polar lipid, or a combination thereof.

19. The method of claim 13, wherein providing the microbial detection device comprises providing the matrix that further includes at least one pH buffer.

20. A method of making a microbial detection device, the method comprising:
    providing a first liposome encapsulating a first destabilizing compound, wherein the first liposome destabilizes in response to a byproduct of microbial metabolism to release the first destabilizing compound from the first liposome;
    providing a second liposome capable of being destabilized by the first destabilizing compound released from the first liposome, wherein the second liposome encapsulates a second destabilizing compound capable of destabilizing the first liposome when the second liposome is destabilized and releases the second destabilizing compound, wherein the second destabilizing compound is different than the first destabilizing compound; and
    encasing the first liposome and the second liposome with a matrix.

21. The method of claim 20, wherein providing the first liposome comprises providing the first destabilizing compound including a bile salt, a lipase, an acid, a base, a cardiolipin, a reactant capable of generating heat through exothermic reaction, a surfactant, ethanol, or a combination thereof.

22. The method of claim 20 wherein providing the second liposome further comprises providing the second destabilizing compound selected from a bile salt, a lipase, an acid, a base, a cardiolipin, a reactant capable of generating heat through exothermic reaction, a surfactant, ethanol, or a combination thereof.

23. The method of claim 20, wherein encasing the first liposome and the second liposome comprises encasing with the matrix including a hydrogel matrix, a polymer matrix, a polysaccharide matrix, a peptide matrix, or a combination thereof.

24. The method of claim 20, wherein encasing the first liposome and the second liposome comprises encasing with the matrix further comprising a microbial food source, agarose, acrylamide gel, gelatin, hyaluronans, chitosans, alginates, collagen, dextran, pectin, carrageenan, polylysine, or a combination thereof.

25. The method of claim 20, wherein providing the first liposome and providing the second liposome comprises providing at least one of the first liposome or the second liposome including a unilamellar liposome or a multilamellar liposome.

26. The method of claim 20, wherein providing the first liposome and providing the second liposome comprises providing at least one of the first liposome or the second liposome including a temperature-sensitive liposome.

* * * * *